(12) United States Patent
Bessho

(10) Patent No.: US 10,602,949 B2
(45) Date of Patent: Mar. 31, 2020

(54) IMAGE PROCESSING APPARATUS, STRESS MEASURING METHOD AND NON-TRANSITORY RECORDING MEDIUM

(71) Applicant: Konica Minolta, Inc., Chiyoda-ku, Tokyo (JP)

(72) Inventor: Ichiro Bessho, Okazaki (JP)

(73) Assignee: Konica Minolta, Inc., Chiyoda-ku, Tokyo (JP)

( * ) Notice: Subject to any disclaimer, the term of this patent is extended or adjusted under 35 U.S.C. 154(b) by 343 days.

(21) Appl. No.: 15/677,432

(22) Filed: Aug. 15, 2017

(65) Prior Publication Data

US 2018/0055396 A1    Mar. 1, 2018

(30) Foreign Application Priority Data

Aug. 23, 2016  (JP) .................. 2016-162946

(51) Int. Cl.

| | | |
|---|---|---|
| *A61B 5/0456* | (2006.01) | |
| *A61B 5/04* | (2006.01) | |
| *A61B 5/00* | (2006.01) | |
| *A61B 5/02* | (2006.01) | |
| *A61B 5/16* | (2006.01) | |
| *G16H 40/67* | (2018.01) | |
| *A61N 1/08* | (2006.01) | |

(52) U.S. Cl.
CPC .......... *A61B 5/0456* (2013.01); *A61B 5/0004* (2013.01); *A61B 5/0022* (2013.01); *A61B 5/0044* (2013.01); *A61B 5/02* (2013.01); *A61B 5/04017* (2013.01); *A61B 5/165* (2013.01); *A61N 1/08* (2013.01); *G16H 40/67* (2018.01)

(58) Field of Classification Search
CPC ... A61B 5/0456; A61B 5/0004; A61B 5/0022; A61B 5/0044; A61B 5/02; A61B 5/04017; A61B 5/165; A61N 1/08; G16H 40/67
See application file for complete search history.

(56) References Cited

FOREIGN PATENT DOCUMENTS

| | | |
|---|---|---|
| JP | 2001-104273 A | 4/2001 |
| JP | 2008-142469 A | 6/2008 |

*Primary Examiner* — Mark Bockelman
(74) *Attorney, Agent, or Firm* — Buchanan Ingersoll & Rooney PC

(57) ABSTRACT

If a job is accepted in the middle of cardiac potential measurement in a state where acquisition of data for stress measurement corresponding to cycles necessary for stress measurement has not been completed, the state of progress of stress measurement is compared with the acceptance timing of the job, and with respect to acceptance of a job for which a time from the acceptance timing of the job to completion of stress measurement on a current measurement object cycle does not exceed a pre-set first setting value, the job is executed after completion of stress measurement in the current measurement cycle, and with respect to acceptance of a job for which a time from the acceptance timing of the job to completion of stress measurement exceeds the first setting value, stress measurement is interrupted and the job is preferentially executed and stress measurement is restarted.

6 Claims, 10 Drawing Sheets

HEART BEAT AND ELECTROCARDIOGRAM

IMAGE PROCESSING APPARATUS, STRESS MEASURING METHOD AND NON-TRANSITORY RECORDING MEDIUM

CROSS-REFERENCE TO RELATED APPLICATIONS

The entire disclosure of Japanese Patent Application No. 2016-162946 filed on Aug. 23, 2016 including description, claims, drawings, and abstract are incorporated herein by reference in its entirety.

BACKGROUND OF THE INVENTION

Field of the Invention

The present invention relates to an image processing apparatus that can measure stress of a user, a stress measuring method and a non-transitory recording medium storing a computer readable program which is a stress measuring program for the apparatus.

Description of the Related Art

A law revising a part of the Industrial Safety and Health Act came into effect on Dec. 1, 2015, and the implementation of stress checks for employees becomes mandatory at business establishments with more than a certain number of employees.

There are also such backgrounds, for instance, MFP (Multi Function Peripheral) which is a multifunctional digital multifunction peripheral having a plurality of functions such as a copy function, a printer function, a facsimile function, a scan function is one of image processing apparatus, and development has been made to provide a function to display a measurement result on an operation panel, and to perform printing and mail transmission, etc., by incorporating a stress measurement device.

The stress measurement is carried out by measuring the cardiac potential by placing fingers of the user on the two electrodes at a predetermined position, as already known. More specifically, as shown in FIG. 10A, R wave, which is a peak value corresponding to one heartbeat of the heart, is detected, while, as shown in FIG. 10B, a heart beat interval (R Wave interval) is measured, and stress can be measured by analyzing the fluctuation frequency of the R wave interval cycle, and the power spectrum integration ratio of low frequency (LF):0.05 to 0.15 Hz and high frequency (HF):0.15 to 0.4 Hz.

(A) of FIG. 11 is a graph showing measurement results of the cardiac potential with time on the horizontal axis and R wave interval on the vertical axis. When this measurement result is frequency analyzed, a waveform in which a high frequency (HF) is superimposed on a low frequency (LF) having periodicity is obtained, as shown in (B) of FIG. 11. Lengths indicated by arrows are low frequency one cycle and high frequency one cycle, respectively. The low frequency approximates a sine wave, and each cycle is repeated with the lapse of time. Then, stress is measured from the ratio of power spectrum integration of low frequency and high frequency.

The cardiac potential is grasped by detecting the biological microvoltage signal of the fingertip (Peak value about 1 mV). However, due to such a microvoltage signal, when noise generating parts of the image processing apparatus, such as a component of the engine system generating low frequency, is normally operated, S/N ratio is deteriorated, which makes an accurate measurement difficult. Especially, engine operation noise during printing operation gives rise to a problem of great noise influence on stress measurement (cardiac potential measurement).

Also, since it is necessary to measure the power spectrum of the fluctuation frequency of the R wave interval period, at least one cycle of the low frequency, which might be about 20 seconds at the maximum, must be continuously measured in the cardiac potential measurement.

As shown in (A) of FIG. 12, in order to avoid the influence of noise, if the stress measurement (cardiac potential measurement) is prioritized, without exception, in a case where the job is accepted at the timing T1 during the stress measurement (cardiac potential measurement), the job is executed after the end timing T 4 of the stress measurement (cardiac potential measurement) as shown in (B) of FIG. 12, and the time from acceptance of the job to completion of execution becomes rather long. To the contrary, as shown in (A) of FIG. 13, in a case of a job being accepted at timing T1 during stress measurement (cardiac potential measurement), the job may be executed while continuing the measurement, as shown in (B) of FIG. 13. However, the data measured in the area S1 after the printing engine operation is affected by noise which may interrupt the measurement. Further, in a case of the execution of the job being prioritized, without exception, by interrupting the cardiac potential measurement at the timing T1, due to the above constraint that the cardiac potential measurement must continuously measure at least one cycle of the low frequency, measured data (data of area S2), which is obtained before acceptance of the job and less than one cycle of the low frequency, is wasted and this is also a problem.

Incidentally, JP 2001-104273 A discloses a body fat measuring device with a weight scale that enables individual body information to be input after measurement of body weight.

Further, JP 2008-142469 A discloses a method in which measured body weight, impedance measurement result, and at least one of sex, race, age, height, body mass index, body fat percentage, and body fat mass are taken as variables for calculating the circumference of the waist with using the previously stored constant values for the variables that have no input.

However, the techniques described in JP 2001-104273 A and JP 2008-142469 A are not the arts relating to cases where a job is accepted during stress measurement. In other words, they do not provide any solution to the above problems in such cases where the job execution was prioritized or where priority is given to the stress measurement, each being prioritized, without exception, when the job is accepted during the stress measurement.

SUMMARY OF THE INVENTION

The present invention has been made in view of such a technical background, and it is an object of the present invention to provide an image processing apparatus and a stress measuring method or program, for solving the problem of lengthy processing time required for the executed job from the acceptance to the completion, which occurs in the case of the stress measurement being prioritized, without exception, when the job is accepted during the stress measurement, and/or the problem of wasting the measured data, which is obtained before acceptance of the job and less than one cycle of the low frequency, by prioritizing the execution of the job without exception.

The abovementioned object is achieved by the following configurations.

(1) To achieve the abovementioned object, according to an aspect, an image processing apparatus reflecting one aspect of the present invention comprises: a job accepting unit configured to accept jobs; a job executing unit configured to execute jobs accepted by the job accepting unit; a measuring unit configured to measure the cardiac potential of a user, thereby acquiring data for stress measurement having periodicity; and a control unit configured to compare the state of progress of stress measurement on a current measurement object cycle with a job acceptance timing if the job accepting unit accepts a job in the middle of cardiac potential measurement of the measuring unit in a state where acquisition of data for stress measurement corresponding to a plurality of cycles necessary for stress measurement has not been completed, and perform control with respect to acceptance of a job for which a time from the acceptance timing of the job to completion of stress measurement on a current measurement object cycle is equal to or smaller than a pre-set first setting value, such that the job executing unit executes the job after completion of stress measurement on the current measurement object cycle, and perform first control with respect to acceptance of a job for which a time from the acceptance timing of the job to completion of stress measurement on a current measurement object cycle exceeds the first setting value, such that stress measurement is interrupted and the job executing unit preferentially executes the job and stress measurement is restarted from the beginning of the interrupted cycle after the job execution is completed.

(2) In the image processing apparatus disclosed in Item (1), the control unit compares a timing of completion of acquisition of data for stress measurement from a final cycle with the job acceptance timing, and performs control with respect to acceptance of a job for which a time from the acceptance timing of the job to completion of acquisition of data for stress measurement from a final cycle is equal to or smaller than a pre-set second setting value, such that the job executing unit executes the job after completion of acquisition of data for stress measurement from the final cycle, and performs the first control with respect to acceptance of a job for which the time from the acceptance timing of the job to completion of acquisition of data for stress measurement from a final cycle exceeds the second setting value.

(3) In the image processing apparatus disclosed in Item (1) or (2), data for stress measurement having periodicity which is acquired by the measuring unit is the fluctuation cycle of an R wave interval which is detected in cardiac potential measurement, and the control unit estimates a value corresponding to one cycle of the fluctuation cycle from a result of R wave interval measurement by sine-wave approximation, and uses the estimate value corresponding to one cycle or a value which is an integral multiple of the estimate value to determine a timing of completion of stress measurement on a current measurement object cycle or a timing of completion of acquisition of data for stress measurement from a final cycle.

(4) To achieve the abovementioned object, according to an aspect, a stress measuring method for an image processing apparatus reflecting one aspect of the present invention comprises: a job accepting step of accepting jobs; a job executing step of executing jobs accepted by the job accepting step; a measuring step of measuring the cardiac potential of a user, thereby acquiring data for stress measurement having periodicity; and a control step of comparing the state of progress of stress measurement on a current measurement object cycle with a job acceptance timing if a job is accepted in the job accepting step in the middle of cardiac potential measurement of the measuring step in a state where acquisition of data for stress measurement corresponding to a plurality of cycles necessary for stress measurement has not been completed, and performing control with respect to acceptance of a job for which a time from the acceptance timing of the job to completion of stress measurement on a current measurement object cycle is equal to or smaller than a pre-set first setting value, such that the job is executed in the job executing step after completion of stress measurement on the current measurement object cycle, and performing first control with respect to acceptance of a job for which a time from the acceptance timing of the job to completion of stress measurement on a current measurement object cycle exceeds the first setting value, such that stress measurement is interrupted and the job is preferentially executed in the job executing step and stress measurement is restarted from the beginning of the interrupted cycle after the job execution is completed.

(5) The stress measuring method for an image processing apparatus disclosed in Item (4), in the control step, a timing of completion of acquisition of data for stress measurement from a final cycle is compared with a job acceptance timing, and with respect to acceptance of a job for which a time from the acceptance timing of the job to completion of acquisition of data for stress measurement from a final cycle is equal to or smaller than a pre-set second setting value, control is performed such that the job is executed in the job executing step after completion of acquisition of data for stress measurement from the final cycle, and with respect to acceptance of a job for which a time from the acceptance timing of the job to completion of acquisition of data for stress measurement from a final cycle exceeds the second setting value, the first control is performed.

(6) The stress measuring method for an image processing apparatus disclosed in Item (4) or (5), data for stress measurement having periodicity which is acquired by the measuring step is the fluctuation cycle of an R wave interval which is detected in cardiac potential measurement, and in the control step, a value corresponding to one cycle of the fluctuation cycle is estimated from a result of R wave interval measurement by sine-wave approximation, and the estimate value corresponding to one cycle or a value which is an integral multiple of the estimate value is used to determine a timing of completion of stress measurement on a current measurement object cycle or a timing of completion of acquisition of data for stress measurement from a final cycle.

(7) To achieve the abovementioned object, according to an aspect, a non-transitory recording medium storing a computer readable program which is a stress measuring program reflecting one aspect of the present invention makes a computer of an image processing apparatus perform the followings: a job accepting step of accepting jobs; a job executing step of executing jobs accepted by the job accepting step; a measuring step of measuring the cardiac potential of a user, thereby acquiring data for stress measurement having periodicity; and a control step of comparing the state of progress of stress measurement on a current measurement object cycle with a job acceptance timing if a job is accepted in the job accepting step in the middle of cardiac potential measurement of the measuring step in a state where acquisition of data for stress measurement corresponding to a plurality of cycles necessary for stress measurement has not been completed, and performing control with respect to acceptance of a job for which a time from the acceptance timing of the job to completion of stress measurement on a current measurement object cycle is equal to or smaller than a pre-set first setting value, such that the job is executed in the job executing step after completion of stress measurement on the current measurement object cycle, and performing first control with respect to acceptance of a job for which a time from the acceptance timing of the job to completion of stress measurement on a current measurement object cycle exceeds the first setting value, such that stress measurement is interrupted and the job is preferentially executed in the job executing step and stress measurement is restarted from the beginning of the interrupted cycle after the job execution is completed.

(8) In the stress measuring program disclosed in Item (7), the stress measuring program performs control such that, in the control step, the computer performs a process of comparing a timing of completion of acquisition of data for stress measurement from a final cycle with a job acceptance timing, and performing control with respect to acceptance of a job for which a time from the acceptance timing of the job to completion of acquisition of data for stress measurement from a final cycle is equal to or smaller than a pre-set second setting value, such that the job is executed in the job executing step after completion of acquisition of data for stress measurement from the final cycle, and performing the first control with respect to acceptance of a job for which the time from the acceptance timing of the job to completion of acquisition of data for stress measurement from a final cycle exceeds the second setting value.

(9) In the stress measuring program disclosed in Item (7) or (8), data for stress measurement having periodicity which is acquired by the measuring step is the fluctuation cycle of an R wave interval which is detected in cardiac potential measurement, and the stress measuring program performs control such that, in the control step, the computer performs a process of estimating a value corresponding to one cycle of the fluctuation cycle from a result of R wave interval measurement by sine-wave approximation, and using the estimate value corresponding to one cycle or a value which is an integral multiple of the estimate value to determine a timing of completion of stress measurement on a current measurement object cycle or a timing of completion of acquisition of data for stress measurement from a final cycle.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Hereinafter, an embodiment of the present invention will be described with reference to the drawings. However, the scope of the invention is not limited to the illustrated examples.

Figure 1:
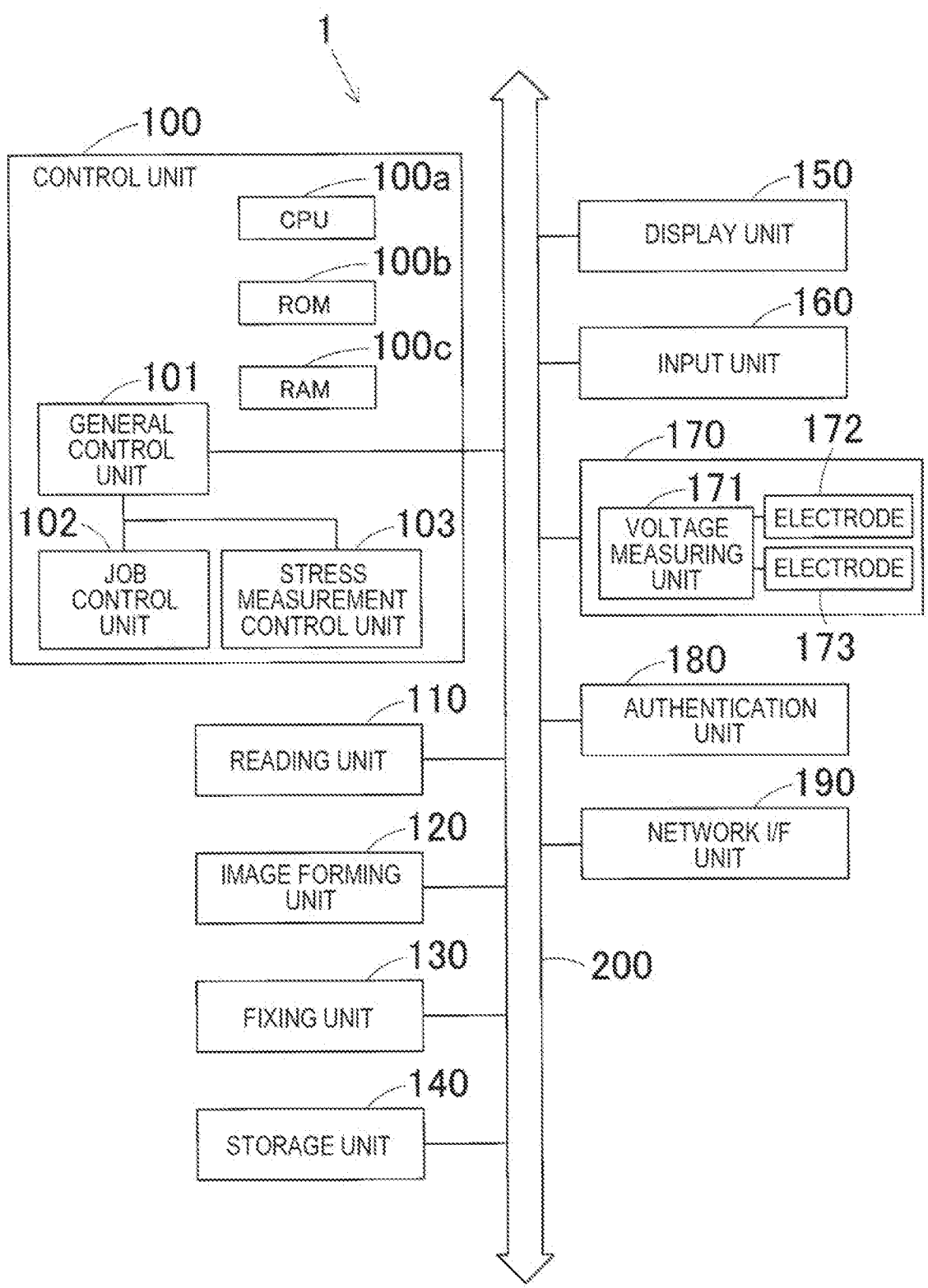
FIG. 1 is a block diagram illustrating the configuration of an image processing apparatus according to an embodiment of the present invention.

FIG. 1 is a block diagram illustrating the configuration of an image processing apparatus according to an embodiment of the present invention.

In the present embodiment, as an image processing apparatus 1, an MFP which is a multifunctional digital image processing apparatus having functions such as a printer function, a facsimile function, and a scan function is used. Hereinafter, the image processing apparatus will also be referred to as the MFP.

As shown in FIG. 1, the MFP 1 includes a control unit 100, a reading unit 110, an image forming unit 120, a fixing unit 130, a storage unit 140, a display unit 150, an input unit 160, a cardiac potential measuring unit 170, an authentication unit 180, a network interface (I/F) unit 190, and so on, which are connected to one another by a system bus 200.

The control unit 100 functionally includes a general control unit 101, a job control unit 102, and a stress measurement control unit 103. The general control unit 101 generally controls the whole of the MFP 1. The job control unit 102 controls the functions such as the copy function, the printer function, the scan function, and the facsimile function to perform control relative to acceptance and execution of jobs. The stress measurement control unit 103 calculates the level of stress on the basis of measurement results of the cardiac potential measuring unit 170.

The control unit 100 includes a CPU 100a, a ROM 100b, and a RAM 100c. The CPU 100a executes programs stored in the ROM 100b and the like, thereby controlling the whole of the MFP 1. The ROM 100b is for storing programs to be executed by the CPU 100a, and other data. The RAM 100c is a memory usable as a work area when the CPU 100a executes programs, and is for temporarily storing programs, and data and the like for executing the programs. Also, the general control unit 101, the job control unit 102, and the stress measurement control unit 103 are component parts which are functionally implemented by the operation of the CPU 100a.

The reading unit 110 includes a scanner and so on, and is a unit for scanning documents set on platen glass, thereby reading the documents, and converting the read documents into image data.

The image forming unit 120 is a unit for printing copy images generated from image data of documents read by the reading unit 110 and print data, on sheets, and the fixing unit 130 is a unit for fixing copy images printed on sheets. The reading unit 110, the image forming unit 120, the fixing unit 130, and so on form a job executing unit for executing copy jobs and the image forming unit 120, the fixing unit 130, and so on form a job executing unit for executing print jobs.

The storage unit 140 is configured with a hard disk and so on, and is for storing programs and a variety of data such as authentication information usable for authentication when the user logs in and cardiac potential measurement data.

The display unit 150 is configured, for example, with a liquid crystal screen, and displays messages, various operation screens, stress level measurement results, and so on.

The input unit 160 is used when the user inputs setting values to instruct job execution or inputs user-specific parameters and the like to measure the level of stress, and is configured with a touch panel or hard keys such as numeric keys and a start button.

The cardiac potential measuring unit 170 is a unit for measuring the cardiac potential of the user in order to measure the level of stress of the user, and includes a pair of electrodes 172 and 173, and a voltage measuring unit 171 for detecting the biological microvoltage signal between fingertips in a state where the user puts both hands on the electrodes 172 and 173, respectively.

The authentication unit 180 is a unit for performing authentication when the user logs in to the MFP 1, and the network interface unit 190 is a unit for performing data communication with external devices such as other MFPs and user's terminal devices through a network.

Now, the operation of the MFP 1 shown in FIG. 1 will be described.

Figure 2:
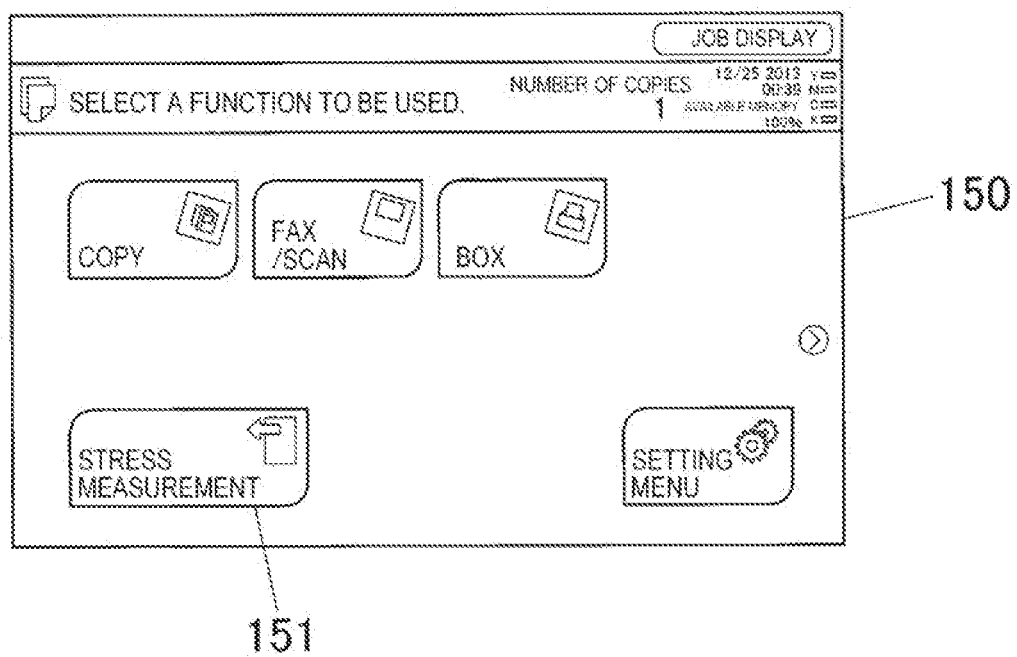
FIG. 2 is a view illustrating an initial screen which is displayed if a user logs in to the image processing apparatus.
Figure 3:
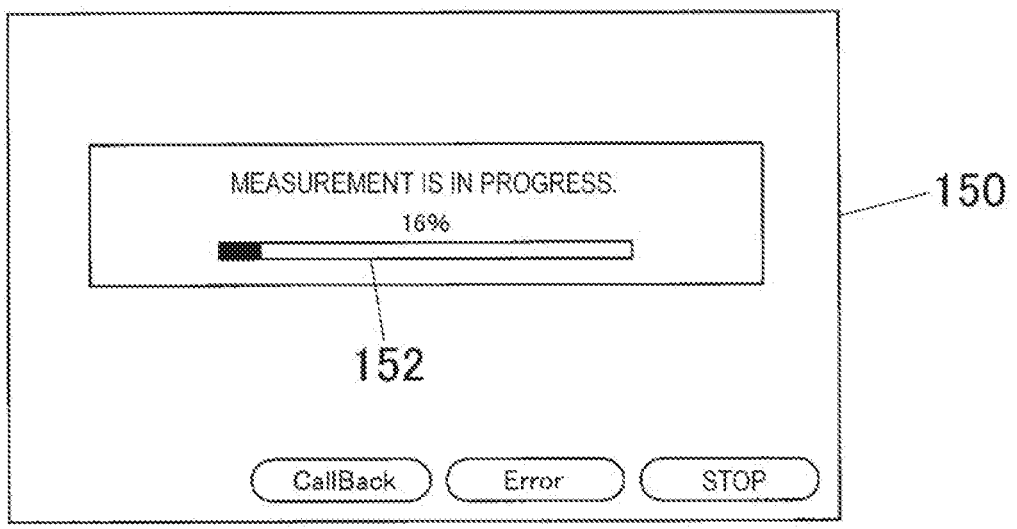
FIG. 3 is a view illustrating a screen which is displayed during cardiac potential measurement.

If the user performs authentication to log in to the MFP 1, the initial screen shown in FIG. 2 is displayed on the display unit 150. In a case where the user wants to perform stress measurement, if the user presses a "stress measurement" button 151 displayed on the screen, and puts both hands on the electrodes 172 and 173, the cardiac potential is measured by the voltage measuring unit 171. During the measurement, as shown in FIG. 3, a character string "MEASUREMENT IS IN PROGRESS" and an indicator 152 indicating the rate of progression of measurement are displayed on the display unit 150.

Figure 11:
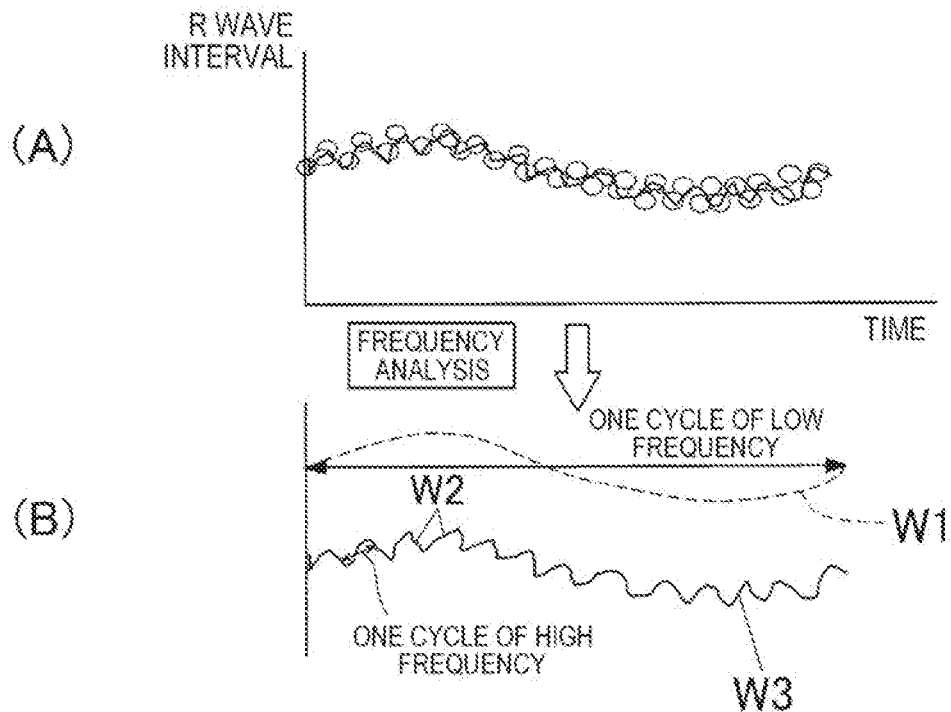
FIG. 11 is a view illustrating waveforms obtained by performing frequency analysis on cardiac potential measurement results.
Figure 12:
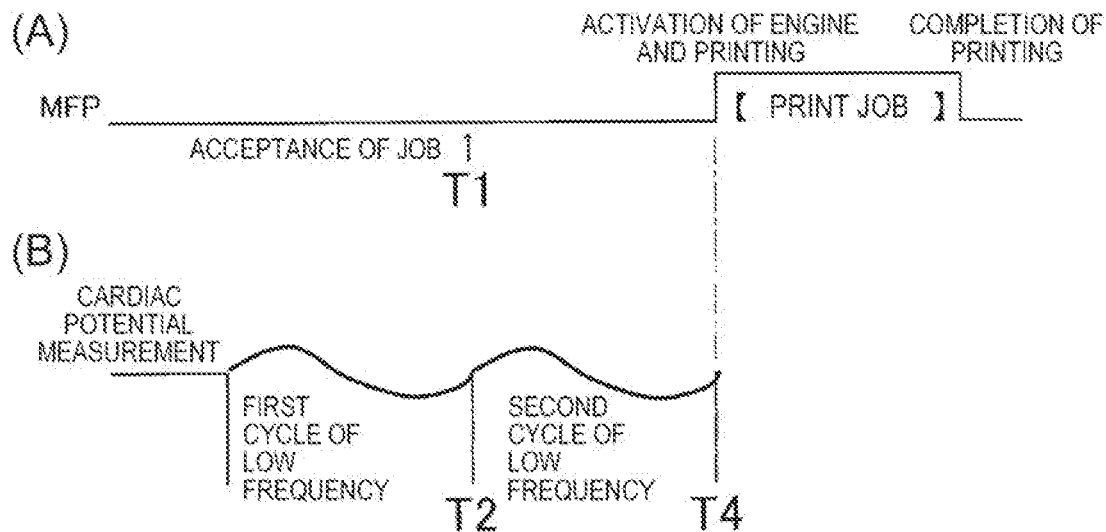
FIG. 12 is a view for explaining a problem of the related art in a case where a job has been accepted during cardiac potential measurement.
Figure 13:
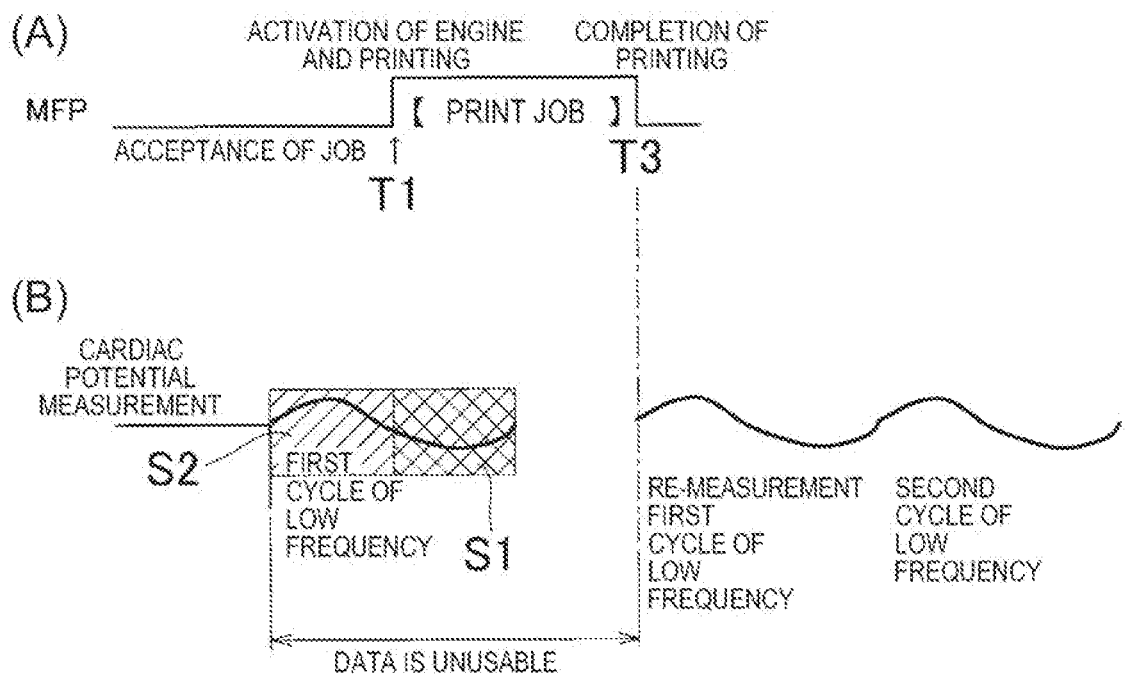
FIG. 13 is a view for explaining a problem of the related art in a case where a job has been accepted during cardiac potential measurement.

The stress measurement control unit 103 performs frequency analysis on the cardiac potential measurement result. As a result, as shown in (B) of FIG. 11, high frequency (HF) is superimposed on low frequency (LF) having periodicity.

In a case where the MFP 1 accepts a print job from a user's terminal device configured, for example, with a personal computer in the middle of stress measurement (cardiac potential measurement), if the job is executed as it is, noise generated during the execution adversely affects the cardiac potential measurement. For this reason, it is necessary to execute either the measurement or the job. In measuring stress from the power spectrum integration ratio, data corresponding to a plurality of cycles of the low frequency is necessary. However, since it takes a long time to acquire measurement data corresponding to a plurality of cycles, if the print job is executed after stress measurement finishes, it may take along time to complete the print job. Meanwhile, if the cardiac potential measurement is interrupted, and the print job is immediately executed, even though measurement on one current measurement object cycle is almost done, the measurement should be interrupted. For this reason, measurement continuity is lost, and the measurement data already acquired with respect to the corresponding cycle becomes useless.

For this reason, in the present embodiment, in a case where the MFP 1 accepts a print job or the like in the middle of stress measurement (cardiac potential measurement), the following control is performed. This will be described with reference to FIGS. 4 to 6. Also, the following description will be made on the assumption that data corresponding to two cycles of the low frequency is required; however, the present invention is not limited to data corresponding to two cycles.

As shown in FIGS. 4A and 4B, after cardiac potential measurement starts, if a print job is accepted at a timing T1 in the middle of measurement of data corresponding to one cycle of the low frequency, the job control unit 102 compares a time T from the job acceptance timing T1 to a timing T2 of completion of measurement on the first cycle which is a current measurement object with a setting value t1 set in advance. In a case where the time T is larger than the setting value t1, since it is considered that it will take a long time to complete measurement on the first cycle, the cardiac potential measurement is interrupted, and the print job is immediately executed. In other words, a printing engine is activated, and performs printing. Therefore, the print job is executed in a short time. In this case, although cardiac potential data measured until the acceptance of the job becomes useless, since it is considered that the amount of measured data is small, the print job is prioritized. Also, determination of the measurement completion timing T2 will be described below.

If it is assumed that the print job has been completed at a timing T3, from the timing T3, cardiac potential measurement is re-performed from the first cycle.

Figure 5:
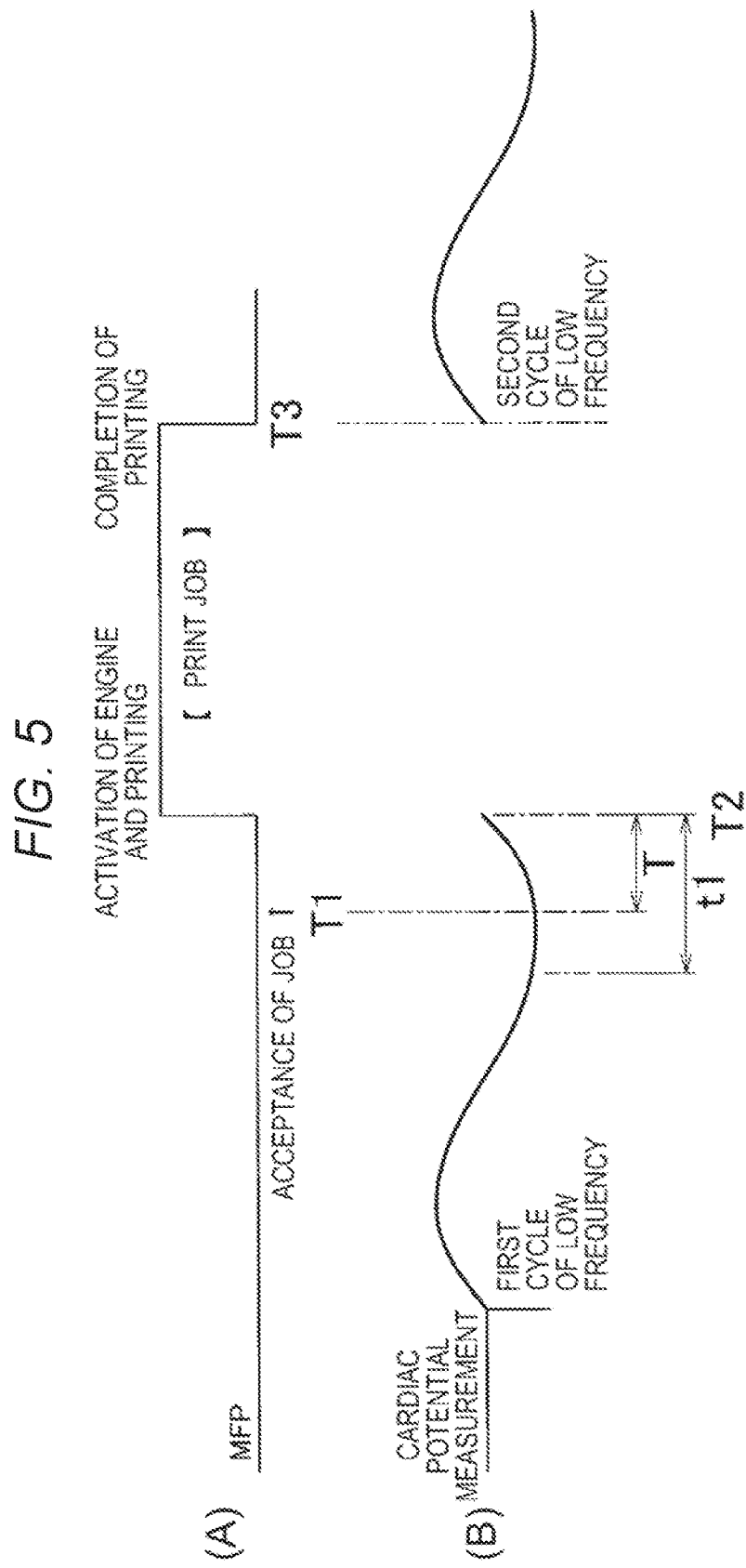
FIG. 5 is a view for explaining an operation which is performed in a case where measurement is prioritized when a print job has been accepted during one cycle of a low frequency after start of cardiac potential measurement.

Meanwhile, as shown in (A) and (B) of FIG. 5, in a case where the time T from the timing T1 in the middle of one cycle of the low frequency when the print job was accepted to the timing T2 of completion of measurement on the first cycle which is the current measurement object is equal to or smaller than the setting value t1, since it is considered that it will take a short time to complete measurement on the first cycle, the cardiac potential measurement is continued to complete measurement on the first cycle. Therefore, it is possible to use the measurement data of the first cycle in stress measurement, without making the measurement data useless. After the measurement on the first cycle is completed, the measurement is interrupted without performing measurement on the second cycle, and the print job is executed. As described above, since the print job is started after the measurement on the first cycle is completed, as compared to a case where it is impossible to execute the job until measurement on every object cycle is completed, it is possible to reduce the waiting time of the print job.

If it is assumed that the print job has been completed at the timing T3, from the timing T3, cardiac potential measurement is restarted. Since the measurement on the first cycle has been completed, the measurement is restarted from the second cycle.

As described above, in the present embodiment, the time T from the job acceptance timing T1 to the timing T2 of completion of measurement on the first cycle which is the current measurement object is compared with the setting value t1 set in advance, and in a case where the time T is larger than the setting value t1, the cardiac potential measurement is interrupted, and the print job is immediately executed; whereas in a case where the time T is equal to or smaller than the setting value t1, the cardiac potential measurement is continued to complete measurement on the first cycle, and then the print job is executed. In other words, it is possible to suppress cardiac potential measurement data from becoming useless while avoiding prolongation of the waiting time of job execution.

Figure 4:
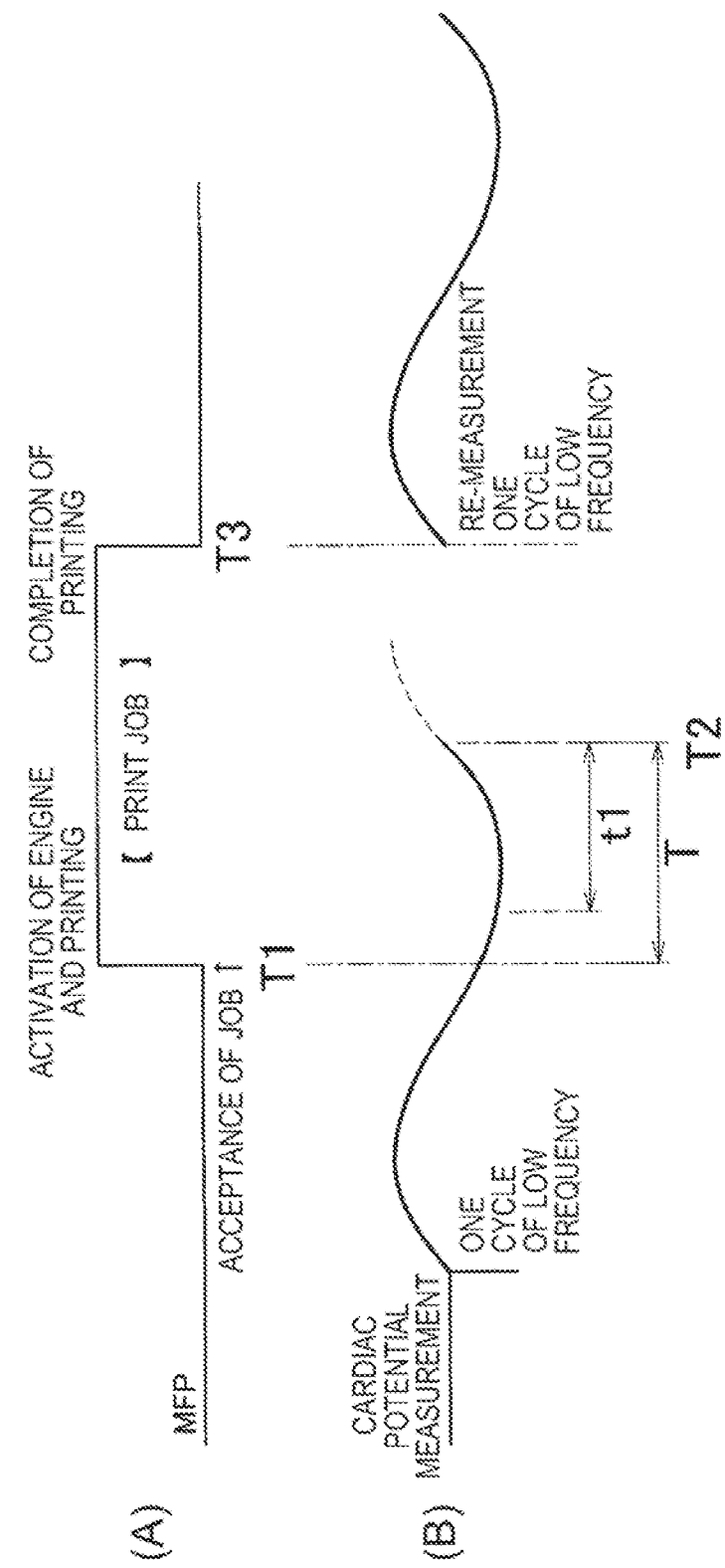
FIG. 4 is a view for explaining an operation which is performed in a case where a print job is prioritized when the print job has been accepted during one cycle of a low frequency after start of cardiac potential measurement.

Also, FIGS. 4 and 5 show the case where a print job has been accepted at a timing in the middle of one cycle of the low frequency after start of cardiac potential measurement; however, in a case where a print job has been received at a timing in the middle of the second cycle, a similar operation is performed. In this case, a time T from the job acceptance timing to a timing of completion of measurement on the second cycle which is the current measurement object may be compared with the setting value t1. Even in a case where the number of cycles necessary in measurement is 3 or more, a similar operation is performed.

Figure 6:
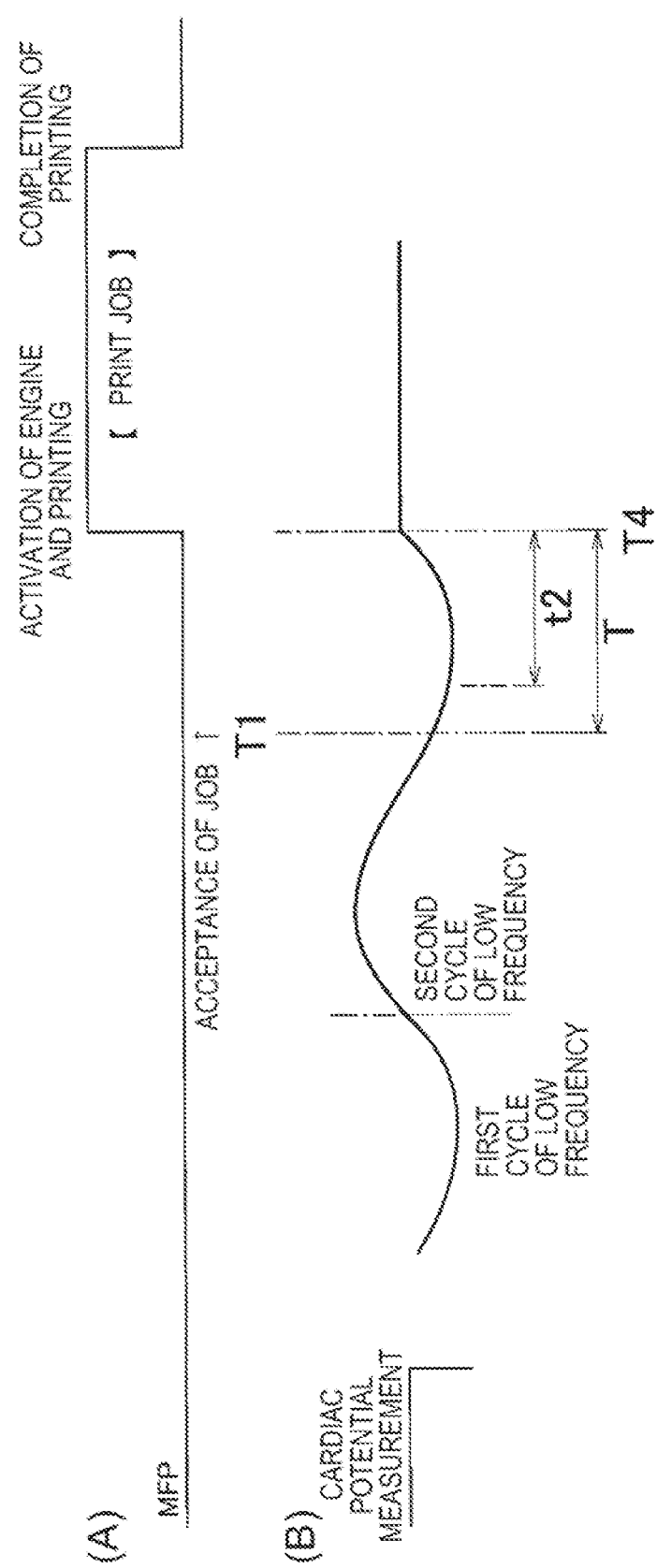
FIG. 6 is a view for explaining another embodiment of the present invention.

FIG. 6 is a view for explaining another embodiment of the present invention. In a case where a job is accepted in the middle of cardiac potential measurement on the final cycle, though it may take a long time to complete the measurement, completion of the measurement may be prioritized.

For this reason, in the present embodiment, in view of the time T from the job acceptance timing T1 to a timing T4 of completion of cardiac potential measurement, the time T is compared with a setting value t2. Although not limited, the setting value t2 is set to a value larger than the setting value t1. Then, in a case where the time T is equal to or smaller than the setting value t2, completion of the cardiac potential measurement is prioritized, and thus the measurement is continued. Therefore, in this case, the user can see the stress measurement result early. Also, similarly in the case where the job has been accepted in the middle of the first cycle, in a case where the time T from the job acceptance timing T1 to the timing T4 of completion of the cardiac potential measurement is larger than the setting value t2, as described with reference to FIGS. 4 and 5, the time T is compared with the setting value t1, and the abovedescribed process is performed.

Figure 7:
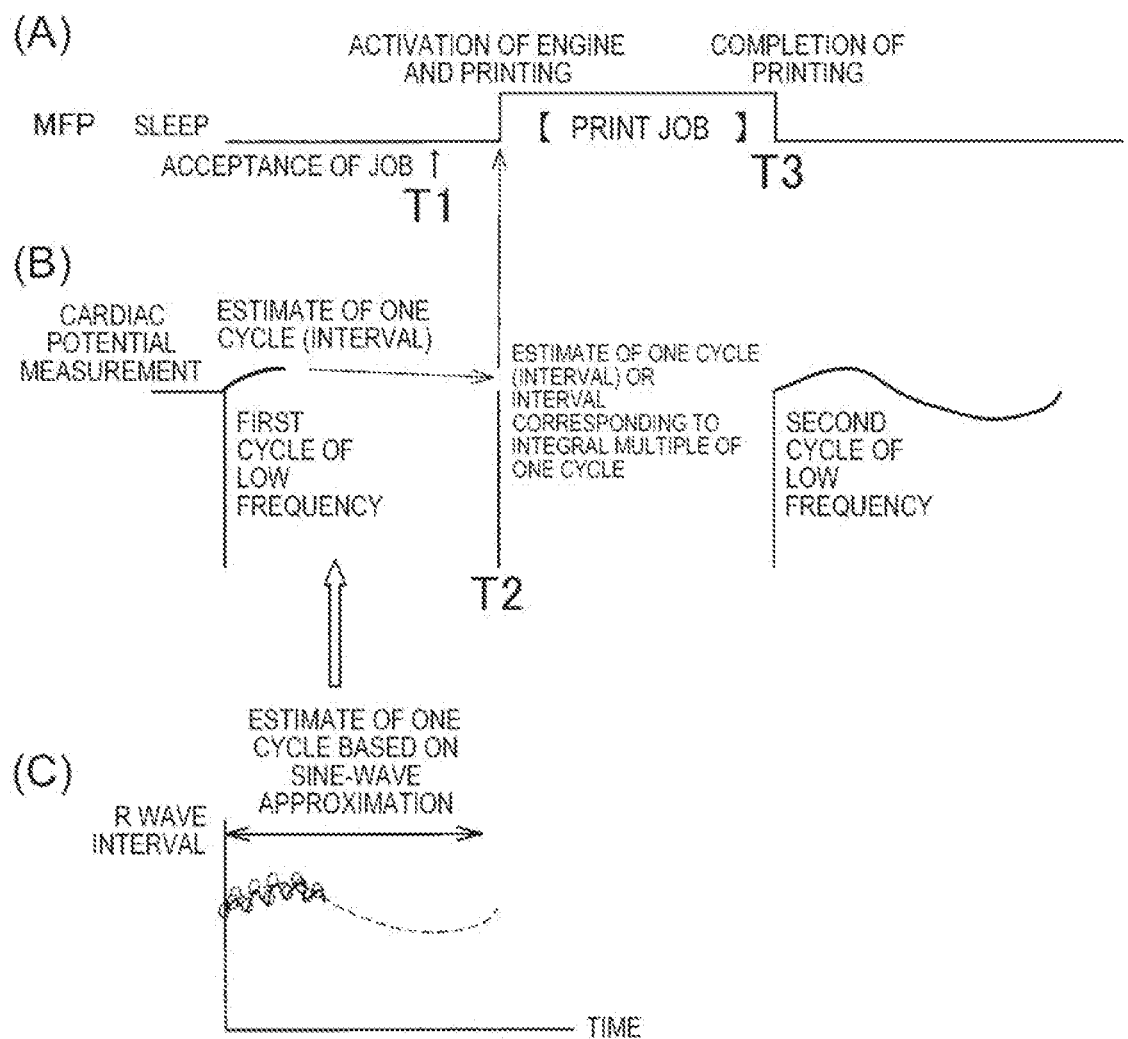
FIG. 7 is a view for explaining a method of determining a timing of completion of measurement on a current measurement object cycle.

FIG. 7 is a view for explaining a method of determining the timing T2 of completion of measurement on the current measurement object cycle or the timing T4 of completion of stress measurement.

In the present embodiment, as shown in (C) of FIG. 7, the R wave interval of the cardiac potential is measured, and a value corresponding to one cycle in the fluctuation cycle of the R wave interval is estimated from the measurement data when the job has been accepted. The estimation uses sine-wave approximation. Further, as shown in (B) of FIG. 7, the estimate value corresponding to one cycle is used to determine the timing T2 of completion of measurement on one cycle, or a value which is two times the estimate value is used to determine the timing of completion of measurement on two cycles. In other words, the estimate value corresponding to one cycle or the value which is the integral multiple of the estimate value is used to determine a timing of completion of stress measurement on the current measurement object cycle or a timing of completion of acquisition of data for stress measurement from the final cycle, and the determined timing is compared with the job acceptance timing T1. Also, when the timing T2 of completion of stress measurement on the current measurement object cycle comes, if a condition "T2−T1≤t1" is satisfied, as shown in (A) of FIG. 7, execution of the print job is started as described above.

Also, although fluctuation cycles depend on users or physical conditions, if estimation as described above is used, it is possible to easily and accurately estimate the timing of completion of measurement on each cycle.

Figure 8:
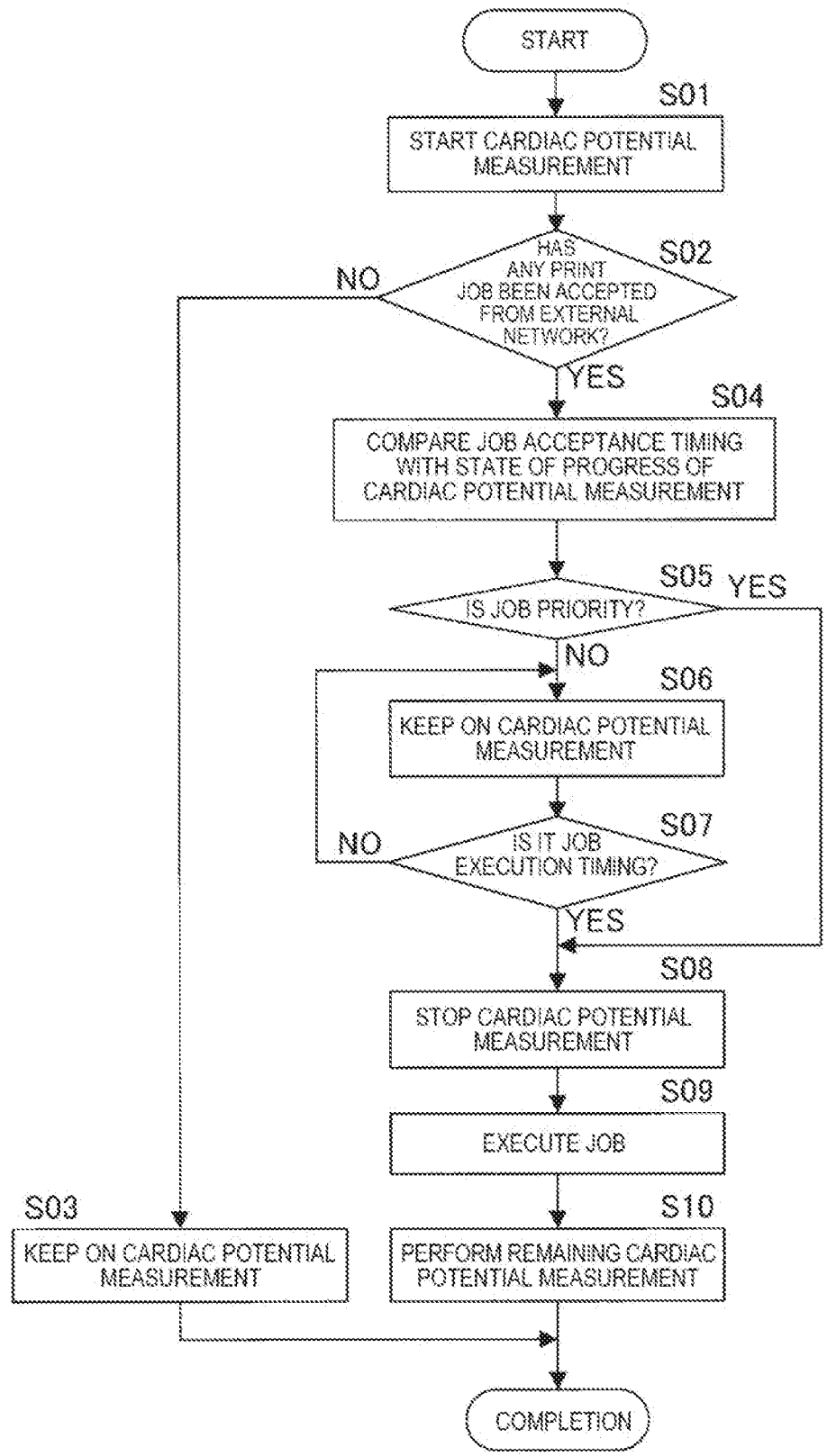
FIG. 8 is a flow chart illustrating an operation which is performed when the process described with reference to FIGS. 4 and 5 is performed.

FIG. 8 is a flow chart illustrating an operation which is performed in a case of performing the process described with reference to FIGS. 4 and 5. The CPU 100*a* of the MFP 1 operates according to an operation program stored in a recording medium such as the ROM 100*b*, whereby the abovementioned operation is performed.

After cardiac potential measurement is started in STEP S01, in STEP S02, whether any print job has been accepted from an external network is checked. In a case where any print job has not been accepted ("NO" in STEP S02), in STEP S03, the cardiac potential measurement is continued as it is.

In a case where a print job has been accepted ("YES" in STEP S02), in STEP S04, the state of progress of the cardiac potential measurement is compared with the job acceptance timing. In other words, whether the time from the acceptance timing T1 of the print job to the timing T2 of completion of measurement on the current measurement object cycle is equal to or smaller than the setting value t1 or not is determined.

In STEP S05, whether the time T is equal to or smaller than the setting value t1 or not, i.e. whether the job is prioritized is determined. In a case where the job is not prioritized ("NO" in STEP S05), in STEP S06, the cardiac potential measurement is continued, and in STEP S07, whether the execution timing of the job has come or not, i.e. whether the cardiac potential measurement on the corresponding cycle has finished is determined. If the execution timing of the job has not come ("NO" in STEP S07), the process returns to STEP S06, and the cardiac potential measurement is continued. If the execution timing of the job has come ("YES" in STEP S07), in STEP S08, the cardiac potential measurement is interrupted. At this time, since measurement data corresponding to one cycle when the job was accepted is continuously acquired, the data does not become useless. Also, in a case where a job has been accepted in the middle of data measurement on the final cycle, the measurement is completed.

Subsequently, after the job is executed in STEP S09, in STEP S10, in a case where the remaining cardiac potential measurement is necessary, the corresponding measurement is performed.

In a case where it is determined in STEP S05 that the time T from the acceptance timing T1 of the print job to the timing T2 of completion of measurement on the current measurement object cycle is larger than the setting value t1, i.e. the job is prioritized, the process proceeds to STEP S08, and the cardiac potential measurement is immediately interrupted, and in STEP S09, the job is executed. Subsequently, in STEP S10, the remaining cardiac potential including measurement data of the cycle when the job was accepted is measured.

Figure 9:
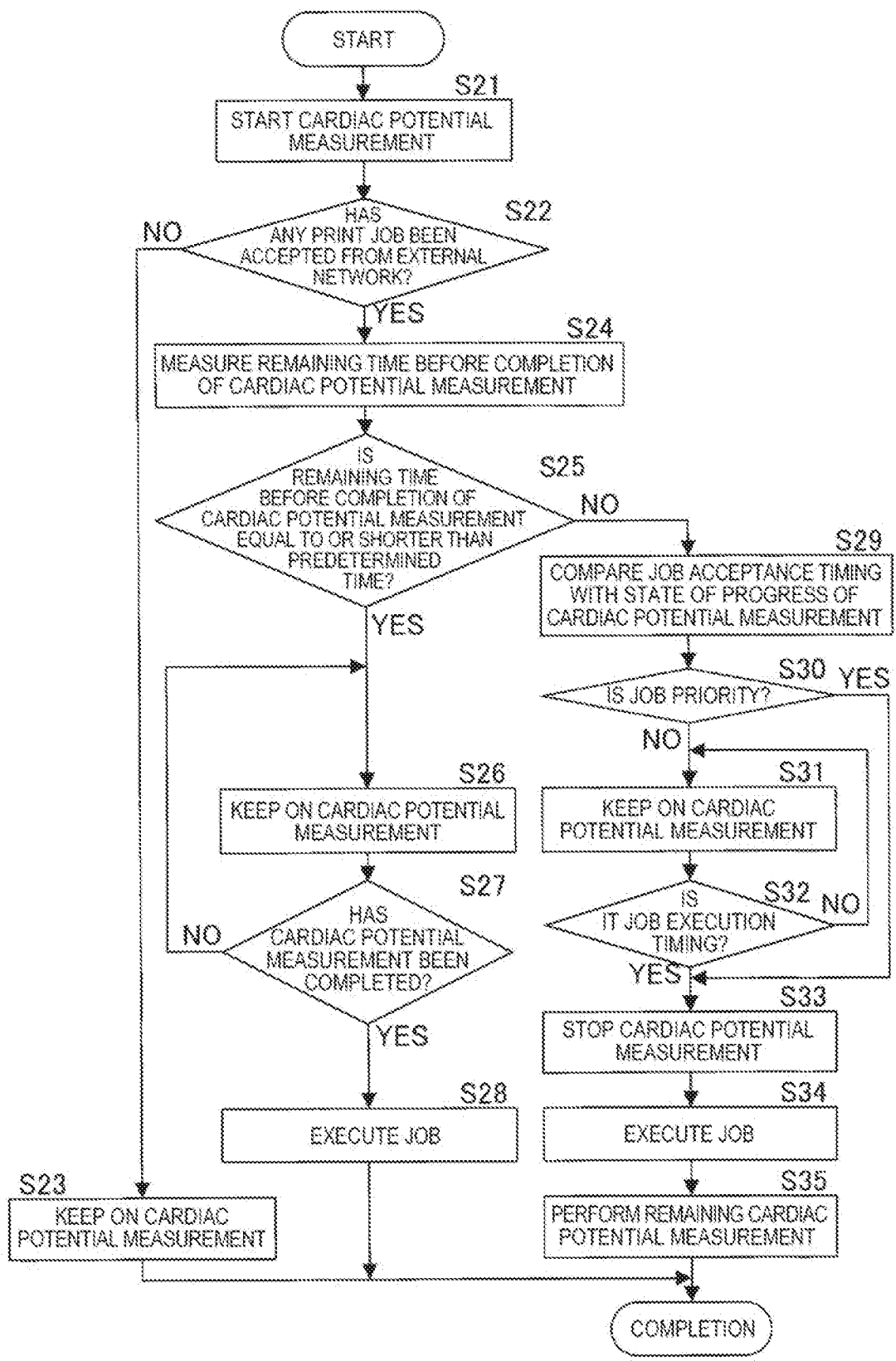
FIG. 9 is a flow chart illustrating an operation which is performed when the process described with reference to FIG. 6 is performed.
Figure 10A:
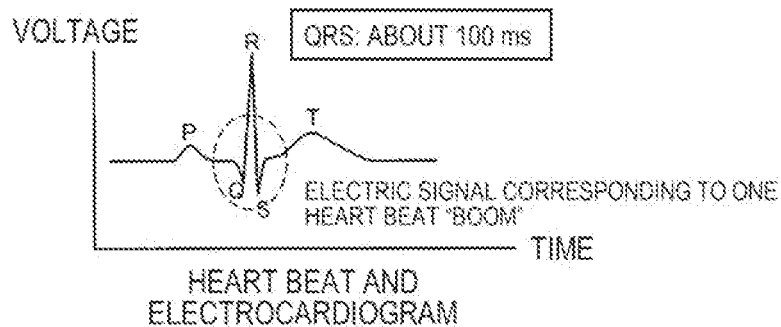
FIGS. 10A and 10B are a view for explaining cardiac potential measurement.
Figure 10B:
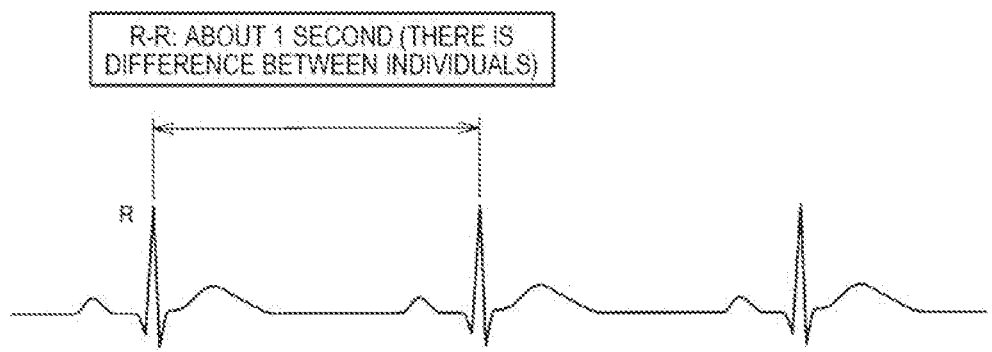

FIG. 9 is a flow chart illustrating an operation which is performed in a case where the MFP 1 performs the process described with reference to FIG. 6. The CPU 100*a* of the MFP 1 operates according to an operation program stored in a recording medium such as the ROM 100*b*, whereby the abovementioned operation is performed.

After cardiac potential measurement is started in STEP S21, in STEP S22, whether any print job has been accepted from an external network is checked. In a case where any print job has not been accepted ("NO" in STEP S22), in STEP S23, the cardiac potential measurement is continued as it is.

In a case where a print job has been accepted ("YES" in STEP S22), in STEP S24, the timing of completion of the cardiac potential measurement is determined, and the time from the job acceptance timing to the timing of completion of the cardiac potential measurement, i.e. the remaining time T of the cardiac potential measurement is determined. Subsequently, in STEP S25, whether the remaining time T is equal to or smaller than a setting time t2 or not is determined. If the remaining time T is equal to or smaller than the setting time t2 ("YES" in STEP S25), in STEP S26, the cardiac potential measurement is continued as it is, and in STEP S27, whether the cardiac potential measurement has been completed or not is determined. If the cardiac potential measurement has not been completed ("NO" in STEP S27), the process returns to STEP S26. If the cardiac potential measurement has been completed ("YES" in STEP S27), in STEP S28, the job is executed.

If it is determined in STEP S25 that the remaining time T is larger than setting time t2 ("NO" in STEP S25), in STEP S29, the state of progress of the cardiac potential measurement is compared with the job acceptance timing. In other words, whether the time from the acceptance timing T1 of the print job to the timing T2 of completion of measurement on the current measurement object cycle is equal to or smaller than the setting value t1 or not is determined.

In STEP S30, whether the time T is equal to or smaller than the setting value t1 or not, i.e. whether the job is prioritized is determined. In a case where the job is not prioritized ("NO" in STEP S30), in STEP S31, the cardiac potential measurement is continued, and in STEP S32, whether the execution timing of the job has come or not, i.e. whether the cardiac potential measurement on the corresponding cycle has finished is determined. If the execution timing of the job has not come ("NO" in STEP S32), the process returns to STEP S31. If the execution timing of the job has come ("YES" in STEP S32), in STEP S33, the cardiac potential measurement is interrupted. At this time, since measurement data corresponding to one cycle when the job was accepted is continuously acquired, the data does not become useless.

Subsequently, after the job is executed in STEP S34, in STEP S35, the remaining cardiac potential measurement is performed.

In a case where it is determined in STEP S30 that the time T from the acceptance timing T1 of the print job to the timing T2 of completion of measurement on the current measurement object cycle is larger than the setting value t1, i.e. the job is prioritized, the process proceeds to STEP S33, and the cardiac potential measurement is immediately interrupted, and in STEP S34, the job is executed. Subsequently, in STEP S35, the remaining cardiac potential including measurement data of the cycle when the job was accepted is measured.

According to the embodiments disclosed in Items (1) and (4), if a job is accepted in the middle of cardiac potential measurement in a state where acquisition of data for stress measurement corresponding to a plurality of cycles necessary for stress measurement has not been completed, the state of progress of stress measurement on a current measurement object cycle is compared with the acceptance timing of the job, and with respect to acceptance of a job for which a time from the acceptance timing of the job to completion of stress measurement on a current measurement object cycle is equal to or smaller than the pre-set first setting value, the job is executed after completion of stress measurement on the current measurement object cycle, and with respect to acceptance of a job for which a time from the acceptance timing of the job to completion of stress measurement on a current measurement object cycle exceeds the first setting value, stress measurement is interrupted and the job is preferentially executed and stress measurement is restarted from the beginning of the interrupted cycle after the job execution is completed. Therefore, as compared to a case where stress measurement (cardiac potential measurement) is prioritized without exception, it is possible to reduce a time required to complete a job, and as compared to a case where job execution is prioritized without exception, it is possible to reduce the amount of measurement data to become useless.

According to the embodiments disclosed in Items (2) and (5), a timing of completion of acquisition of data for stress measurement from a final cycle is compared with a job acceptance timing, and with respect to acceptance of a job for which a time from the acceptance timing of the job to completion of acquisition of data for stress measurement from a final cycle is equal to or smaller than the pre-set second setting value, the job is executed after completion of acquisition of data for stress measurement from the final cycle. In other words, in a case where a time remaining before completion of acquisition of data for stress measurement is short, since stress measurement is prioritized, the user performing the stress measurement can acquire the result of stress measurement early. Meanwhile, with respect to acceptance of a job for which a time from the acceptance timing of the job to completion of acquisition of data for stress measurement from a final cycle exceeds the second setting value, since the first control is performed, it is possible to prevent the stress measurement from being continued more than is necessary, thereby preventing execution of the accepted job from being delayed.

According to the embodiments disclosed in Items (3) and (6), the value corresponding to one cycle of the fluctuation cycle is estimated from the result of R wave interval measurement detected in the cardiac potential measurement by sine-wave approximation, and the estimate value corresponding to one cycle or a value which is an integral multiple of the estimate value is used to determine the timing of completion of stress measurement on the current measurement object cycle or the timing of completion of acquisition of data for stress measurement from the final cycle. Therefore, it is possible to easily determine the timing of completion of stress measurement on the current measurement object cycle or the timing of completion of acquisition of data for stress measurement from the final cycle.

According to the embodiment disclosed in Item (7), it is possible to make the computer of the image processing apparatus perform the process of comparing the state of progress of stress measurement on a current measurement object cycle with a job acceptance timing if a job is accepted in the middle of cardiac potential measurement of the measuring step in a state where acquisition of data for stress measurement corresponding to a plurality of cycles necessary for stress measurement has not been completed, and performing control with respect to acceptance of a job for which a time from the acceptance timing of the job to completion of stress measurement on a current measurement object cycle is equal to or smaller than the pre-set first setting value, the job is executed after completion of stress measurement on the current measurement object cycle, and performing the first control with respect to acceptance of a job for which a time from the acceptance timing of the job to completion of stress measurement on a current measurement object cycle exceeds the first setting value, such that stress measurement on the current measurement object cycle is interrupted and a job is preferentially executed and stress measurement is restarted from the beginning of the interrupted cycle after the job execution is completed According to the embodiment disclosed in Item (8), it is possible to perform control such that, in the control step, the computer of the image processing apparatus performs the process of comparing a timing of completion of acquisition of data for stress measurement from a final cycle with a job acceptance timing, and performing control with respect to acceptance of a job for which a time from the acceptance timing of the job to completion of acquisition of data for stress measurement from a final cycle is equal to or smaller than the pre-set second setting value, such that the job is executed in the job executing step after completion of acquisition of data for stress measurement from the final cycle, and performing the first control with respect to acceptance of a job for which a time from the acceptance timing of the job to completion of acquisition of data for stress measurement from a final cycle exceeds the second setting value.

According to the embodiment disclosed in Items (9), it is possible to perform control such that, in the control step, the computer of the image processing apparatus performs the process of estimating a value corresponding to one cycle of the fluctuation cycle from a result of R wave interval measurement by sine-wave approximation, and using the estimate value corresponding to one cycle or a value which is an integral multiple of the estimate value to determine a timing of completion of stress measurement on a current measurement object cycle or a timing of completion of acquisition of data for stress measurement from a final cycle.

Although the present invention has been described and illustrated in detail, it is clearly understood that the same is by way of illustrated and example only and is not to be taken by way of limitation, the scope of the present invention being interpreted by terms of the appended claims.

What is claimed is:

1. An image processing apparatus comprising:
   an image processing job accepting unit accepting image processing jobs;
   an image processing job executing unit executing the image processing jobs accepted by the image processing job accepting unit;
   a measuring unit measuring a cardiac potential of a user, thereby acquiring data for stress measurement having periodicity; and
   a control unit comparing a state of progress of stress measurement on a current measurement object cycle with an image processing job acceptance timing if the image processing job accepting unit accepts an image processing job in a middle of cardiac potential measurement of the measuring unit in a state where acquisition of data for stress measurement corresponding to a plurality of cycles necessary for stress measurement has not been completed, and perform control with respect to acceptance of an image processing job for which a time from the acceptance timing of the image processing job to completion of stress measurement on a current measurement object cycle is equal to or smaller than a pre-set first setting value, such that the image processing job executing unit executes the image processing job after completion of stress measurement on the current measurement object cycle, and perform first control with respect to acceptance of an image processing job for which a time from the acceptance timing of the image processing job to completion of stress measurement on a current measurement object cycle exceeds the first setting value, such that stress measurement is interrupted and the image processing job executing unit preferentially executes the image processing job and stress measurement is restarted from a beginning of the interrupted cycle after the image processing job execution is completed.

2. The image processing apparatus according to claim 1, wherein:
   the control unit compares a timing of completion of acquisition of data for stress measurement from a final cycle with the image processing job acceptance timing, and performs control with respect to acceptance of an image processing job for which a time from the acceptance timing of the image processing job to completion of acquisition of data for stress measurement from a final cycle is equal to or smaller than a pre-set second setting value, such that the image processing job executing unit executes the image processing job after completion of acquisition of data for stress measurement from the final cycle, and performs the first control with respect to acceptance of an image processing job for which the time from the acceptance timing of the image processing job to completion of acquisition of data for stress measurement from a final cycle exceeds the second setting value.

3. The image processing apparatus according to claim 1, wherein:
   data for stress measurement having periodicity which is acquired by the measuring unit is the fluctuation cycle of an R wave interval which is detected in cardiac potential measurement, and
   the control unit estimates a value corresponding to one cycle of the fluctuation cycle from a result of R wave interval measurement by sine-wave approximation, and uses the estimate value corresponding to one cycle or a value which is an integral multiple of the estimate value to determine a timing of completion of stress measurement on a current measurement object cycle or a timing of completion of acquisition of data for stress measurement from a final cycle.

4. A stress measuring method for an image processing apparatus comprising:
   accepting image processing jobs;
   executing the image processing jobs accepted;
   measuring a cardiac potential of a user, thereby acquiring data for stress measurement having periodicity; and
   comparing a state of progress of stress measurement in a current measurement cycle with an image processing job acceptance timing when the image processing job is accepted during a period of measuring the cardiac potential in a state where acquisition of data for stress measurement corresponding to a plurality of cycles necessary for stress measurement has not been completed, and performing control with respect to acceptance of an image processing job for which a time from the acceptance timing of the image processing job to completion of stress measurement on a current measurement object cycle is equal to or smaller than a pre-set first setting value, such that the image processing job is executed after completion of stress measurement on the current measurement object cycle, and performing first control with respect to acceptance of an image processing job for which a time from the acceptance timing of the image processing job to completion of stress measurement on a current measurement object cycle exceeds the first setting value, such that stress measurement is interrupted and the image processing job is preferentially executed, and stress measurement is restarted from the beginning of the interrupted cycle after the image processing job execution is completed.

5. The stress measuring method for an image processing apparatus according to claim 4, wherein:
when a timing of completion of acquisition of data for stress measurement from a final cycle is compared with an image processing job acceptance timing, and with respect to acceptance of an image processing job for which a time from the acceptance timing of the image processing job to completion of acquisition of data for stress measurement from a final cycle is equal to or smaller than a pre-set second setting value, control is performed such that the image processing job is executed after completion of acquisition of data for stress measurement from the final cycle, and with respect to acceptance of an image processing job for which a time from the acceptance timing of the image processing job to completion of acquisition of data for stress measurement from a final cycle exceeds the second setting value, the first control is performed.

6. The stress measuring method for an image processing apparatus according to claim 4, wherein:
the data for stress measurement having the periodicity is a fluctuation cycle of an R wave interval which is detected in cardiac potential measurement, and
a value corresponding to one cycle of the fluctuation cycle is subsequently estimated from a result of R wave interval measurement by sine-wave approximation, and the estimate value corresponding to one cycle or a value which is an integral multiple of the estimate value is used to determine a timing of completion of stress measurement on a current measurement object cycle or a timing of completion of acquisition of data for stress measurement from a final cycle.

* * * * *